United States Patent [19]

Cleaver

[11] 3,934,977

[45] Jan. 27, 1976

[54] REAGENT AND METHOD FOR DETERMINING TOTAL CALCIUM IN BODY FLUIDS

[75] Inventor: Kenneth E. Cleaver, Woodbury, N.J.

[73] Assignee: American Hospital Supply Corporation, Evanston, Ill.

[22] Filed: Aug. 9, 1974

[21] Appl. No.: 496,003

[52] U.S. Cl. .............................. 23/230 B; 252/408
[51] Int. Cl.² ................. G01N 31/22; G01N 33/16
[58] Field of Search .................... 23/230 B; 252/408

[56] References Cited
OTHER PUBLICATIONS

Ferguson et al., Anal. Chem. 36, 796, (1964).

Hackh's Chemical Dictionary, 4th Edn., McGraw-Hill, p. 538 relied on, 1969.

*Primary Examiner*—Robert M. Reese
*Attorney, Agent, or Firm*—Dawson, Tilton, Fallon & Lungmus

[57] ABSTRACT

A colorimetric determination of total calcium in serum and other body fluids comprising the steps of mixing the sample of body fluid with a liquid reagent consisting of 2,7-bis-(4 chloro-2-phosphonobenzeneazo)-1,8-dihydroxynapthalene-3,6-disulfonic acid, commonly known as chlorophosphonazo III, in a buffer system at pH 5.0 to 5.5, and thereafter spectrophotometrically measuring the level of color development. Potassium hydrogen phthalate is disclosed as a component of the buffer system.

7 Claims, No Drawings

REAGENT AND METHOD FOR DETERMINING TOTAL CALCIUM IN BODY FLUIDS

BACKGROUND

In general, existing methodologies for measuring total calcium in biologic fluids involve considerable manipulation of samples and reagents prior to determination of calcium concentration. Gravimetric and titrimetric methods usually require large sample volumes. Colorimetric methods, both manual and automated, commonly involve final readings under highly alkaline conditions; the indicators used for such determinations are unstable at the final pH, thereby requiring reagent dilution with a strong base. Atomic absorption, the methodology recommended by the National Bureau of Standards, is too time consuming to be used in most routine clinical situations.

One commonly-used serum calcium method utilizes cresolphthalein complexone as the indicator. Calcium is dialyzed under acidic conditions into a recipient stream of cresolphthalein complexone solution. A colored complex between calcium and the dye is formed upon the addition of diethylamine which alkalinizes the reaction mixture. The developed color is then measured in a spectrophotometer at 580 nm. In addition to manipulating three separate solutions, the operator must be constantly aware of the condition of the dialyzer membrane. Should the waste solution become acidified through inadvertence or any other reason, deadly hydrogen cyanide gas is generated. Also, practical experience with the system has revealed some problems of drifting baseline and nonreproducibility. Despite these significant disadvantages, such methodology is generally regarded as easier and more predictable than other colorimetric, gravimetric, or titrimetric methods.

Other commercially available procedures also involve handling highly alkaline reagents with the allowable reading (endpoint) being time-dependent. Such procedures nearly always involve an incubation after sample addition and many must be read within a 30 minute time period. In general, commercial procedures for determining total serum calcium do not involve measurements at neutral or acidic conditions.

Ferguson et al., in Analytical Chemistry, Vol. 36, No. 4, 796–799 (April 1964), described the use of chlorophosphonazo III for spectrophotometrically determining calcium and magnesium in non-biologic fluids, specifically, alkaline earth extracts. Unfortunately, the Ferguson et al. teaching that chlorophosphonazo III is a sensitive reagent for selectively determining calcium (and not magnesium) at pH 2.2 is inapplicable to the measurement of calcium in protein-containing body fluids because of the formation of insoluble calcium-protein complexes under such conditions. Subsequent workers, desiring to use chlorophosphonazo III for determining total serum calcium, have therefore developed multiple-step procedures for separating the calcium and protein of the sample before exposing the calcium to the dye. Thus, Howell et al., in Analytical Chemistry, Vol. 38, No. 3, 434–438 (March 1966) disclose first treating the serum sample with tetrabutylammonium oxalate to precipitate all of the calcium from the body fluid. After separation, the precipitate is redissolved in hydrochloric acid and only then is exposed to chlorophosphonazo III.

SUMMARY

One aspect of this invention lies in the discovery that total calcium in protein-containing body fluids may be accurately and rapidly measured with the use of a single chlorophosphonazo III reagent if that reagent is buffered to a pH within the range of 5.0 to 5.5, the preferred pH being approximately 5.4. At that pH, no absorbance from serum magnesium is observed and other common interferences including bilirubin, hemolysis, and phosphates do not affect test results. The single reagent is stable for at least one year at room temperature and, upon mixing with sample, color development remains unchanged for extended periods of time.

At a pH of about 5.4, the competition of calcium binding by serum protein (albumin) is virtually eliminated, especially where the buffer system includes potassium hydrogen phthalate. While the precise reasons for the effectiveness of a potassium hydrogen phthalate buffer may not be fully understood, it is believed that the phthalate buffer aids in the release of calcium from protein binding and the concurrent chelation of calcium with potassium hydrogen phthalate. Because of an equilibrium occurring between the calcium complexed with the potassium hydrogen phthalate and with chlorophosphonazo III, calcium which would otherwise be unavailable because of protein binding is available for reaction with the dye.

The result is a rapid sensitive test for determining total calcium in body fluids. Complete color formation is achieved immediately after sample-reagent mixing; no incubation is necessary. The high sensitivity (25 nanograms of calcium develop approximately 0.45 absorbance) permits the use of only microliter amounts of serum. For serum calcium levels up to 15 milligram percent (15 milligrams per 100 milliliters), linear results are achieved.

Other advantages and objects of the invention will become apparent as the specification proceeds.

DETAILED DESCRIPTION

The reagent consists essentially of an aqueous solution of chlorophosphonazo III with a buffer system of postassium hydrogen phthalate and potassium (or sodium) hydroxide at a pH within the range of 5.0 to 5.5. The preferred range is 5.35 to 5.45, the optimum level being 5.4.

The dye, referred to herein as chlorophosphonazo III, is 2,7-bis-(4 chloro-2-phosphonobenzeneazo)-1,8-dihydroxynapthalene-3,6-disulfonic acid. The amount of chlorophosphonazo III for any given test depends on the volume of the sample to be tested and the concentration of calcium therein, it being understood that the moles of dye should equal or slightly exceed the moles of calcium in the sample. On the assumption that elevated calcium levels in a serum sample would not be expected to exceed 15 milligrams per deciliter, it has been found that effective results can be obtained routinely when 25 microliters of sample are mixed with 3.0 milliliters of color reagent, the latter containing 0.042 milligrams of chlorophosphonazo III and 0.01 grams of potassium hydrogen phthalate per milliliter of reagent. The concentration of potassium hydrogen phthalate is approximately 0.05 Molar, a concentration selected primarily for ease of manufacture and for achieving a level of color development suitable for most spectrophotometers; however, substantial departures from that concentration (i.e., at least ± 25 percent) could be tolerated depending largely on the spectrophotometric equipment used.

Since the test is highly sensitive, it is important to reduce or eliminate possibilities of calcium contamination from glassware used to contain or transport the reagent. Such glassware may be washed with the reagent itself or with a suitable acid such as, for example, dilute hydrochloric acid. Reproducibility studies have shown that the relatively standard deviation for spectrophotometer tubes washed in 6N hydrochloric acid was only 2.8 percent, in comparison with a relative standard deviation of 5.2 percent for tests conducted with tubes in which such washing step was omitted.

As previously indicated, it has been found that the pH of the reagent must be within the range of 5.0 to 5.5 and preferably about 5.4. Above pH 5.5, the competition of serum calcium binding by albumin becomes an appreciable interfering factor and below pH 5.0 it has been found that turbidity arising from protein precipitation occurs when the reagent and sample are intermixed. Furthermore, at levels substantially above pH 6.0, physiological levels of other serum metals, particularly magnesium, adversely affect the test.

The reagent has been found to be stable for over one year at room temperature and at least 260 days at 56° C. After mixing with a sample of body fluid, the reaction mixture has been found to be of stable color development. Specifically, developed absorbance has been found to be stable at room temperature for at least 40 days as long as the system is protected from external calcium contamination. Where extended periods of storage are likely, the color reagent may incorporate a mold inhibitor such as, for example, benzoic acid (1 gram per liter) or any other suitable inhibitor, all as well known in the art.

Spectrophotometric measurements are made at 615 nm versus the reagent blank, and concentrations are determined by comparison with a suitable calcium standard of known calcium value. Because of the high absorbance of the reagent blanks (approximately 0.95A at 615 nm in a 1.0 centimeter cuvette), cuvettes no greater than about 1.20 centimeters in diameter should be used with routine laboratory spectrophotometers. Since such spectrophotometric procedures are otherwise entirely conventional, a further description is believed unnecessary herein.

The reagent and method of the invention is further revealed by the following illustrative examples:

EXAMPLE 1

Linearity of test results with aqueous standards is illustrated from the following table in which each of the absorbance values is the average of four readings. In each case, 25 microliters of sample containing a known calcium value were added to 3.0 milliliters of color reagent prepared by mixing 42 milligrams per liter of chlorophosphonazo III, 10 grams per liter of potassium hydrogen phthalate, and sufficient potassium hydroxide to provide a pH of 5.35 to 5.45.

TABLE 1

| LINEARITY WITH AQUEOUS STANDARDS | |
|---|---|
| Calcium Value (mg/dl) | Absorbance vs. Blank |
| 5.0 | 0.210 ± .008 |
| 6.0 | 0.253 ± .007 |
| 7.5 | 0.311 ± .006 |
| 9.0 | 0.386 ± .003 |
| 10.0 | 0.425 ± .003 |

TABLE 1-continued

| LINEARITY WITH AQUEOUS STANDARDS | |
|---|---|
| Calcium Value (mg/dl) | Absorbance vs. Blank |
| 11.0 | 0.458 ± .007 |
| 12.5 | 0.525 ± .010 |
| 14.0 | 0.591 ± .008 |
| 15.0 | 0.629 ± .008 |

A plotting of the absorbance values reveals that substantially linear results are achieved for calcium values within the range provided.

EXAMPLE 2

Reproducibility tests with serum samples were undertaken during the interval of one day and also over an interval of 10 days. For the single-day reproducibility tests, each serum sample was analyzed 10 times and the values calculated from a standard curve. The results of the single-day tests are shown in the following table:

TABLE 2

| REPRODUCIBILITY WITHIN A SINGLE DAY | | | |
|---|---|---|---|
| | Depressed Serum | Normal Serum | Elevated Serum |
| Calcium Values (mg/dl) | 7.7 | 9.15 | 12.9 |
| Standard Deviation (mg/dl) | ±0.09 | ±0.13 | 0.09 |
| Relative Standard Deviation | 1.2% | 1.4% | 0.7% |

The day-to-day reproducibility studies were completed over 10 working days. Human serum pools were lyophilized in individual vials and reconstituted daily, prior to duplicate readings of each sample. The results of such testing are as follows:

TABLE 3

| | Depressed Serum | Normal Serum | Elevated Serum |
|---|---|---|---|
| Calcium Values (mg/dl) | 6.64 | 9.0 | 13.88 |
| Standard Deviation (mg/dl) | ±0.32 | ±0.18 | ±0.235 |
| Relative Standard Deviation | 4.8% | 2.0% | 1.7% |

While in the foregoing an embodiment of the invention has been disclosed in considerable detail for purposes of illustration, it will be understood by those skilled in the art that many of these details may be varied from the spirit and scope of the invention.

I claim:

1. A method for the rapid determination of total calcium in protein-containing body fluids, comprising the steps of mixing a sample of body fluid with a color reagent consisting essentially of an aqueous solution of chlorophosphonazo III buffered to a pH within the range of 5.0 to 5.5 by a buffer comprising potassium hydrogen phthalate, and thereafter optically comparing the color development of the sample-reagent mixture with that of the same reagent mixed with a standard of known calcium concentration.

2. The method of claim 1 wherein the pH of said color reagent falls within the range of 5.35 to 5.45.

3. The method of claim 1 in which the pH of said color reagent is about 5.4.

4. A reagent for rapidly determining total calcium in a protein-containing body fluid, comprising an aqueous solution of chlorophosphonazo III buffered to a pH within the range of 5.0 to 5.5, said reagent including potassium acid phthalate as part of the buffer system thereof.

5. The reagent of claim 4 in which the buffer system also includes potassium hydroxide.

6. The reagent of claim 4 in which said pH is within a range of 5.35 to 5.45.

7. The reagent of claim 4 in which said pH is about 5.4.

* * * * *